United States Patent [19]

Fate et al.

[11] 4,381,224
[45] Apr. 26, 1983

[54] STEP FUNCTION LEAN BURN OXYGEN SENSOR

[75] Inventors: William A. Fate, Ann Arbor; Robert E. Hetrick, Dearborn Heights, both of Mich.

[73] Assignee: Ford Motor Company, Dearborn, Mich.

[21] Appl. No.: 258,185

[22] Filed: Apr. 27, 1981

[51] Int. Cl.³ ............................................. G01N 27/46
[52] U.S. Cl. ................................. 204/1 T; 204/195 S
[58] Field of Search ........................... 204/1 S, 195 S

[56] References Cited

U.S. PATENT DOCUMENTS

| | | | |
|---|---|---|---|
| 2,999,379 | 9/1961 | Beard et al. | 73/23 |
| 3,100,868 | 8/1963 | McAfee | 324/33 |
| 3,311,454 | 3/1967 | Kemeny et al. | 23/254 |
| 3,347,635 | 10/1967 | McKee | 23/232 |
| 3,654,112 | 4/1972 | Beekmans et al. | 204/195 S |
| 3,698,384 | 10/1972 | Jones | 204/195 S |
| 3,857,771 | 12/1974 | Sternberg | 204/195 B |
| 3,907,657 | 9/1975 | Heijne | 204/195 S |
| 3,923,624 | 12/1975 | Beekmans et al. | 204/195 S |
| 4,101,403 | 7/1978 | Kita et al. | 204/195 S |
| 4,112,893 | 9/1978 | Anzai | 204/195 S |
| 4,121,548 | 10/1978 | Hattori et al. | 123/32 EE |
| 4,135,381 | 1/1979 | Sherwin | 73/23 |
| 4,147,513 | 4/1979 | Bienkowski et al. | 23/232 E |
| 4,148,211 | 4/1979 | Sawa et al. | 73/23 |
| 4,224,113 | 9/1980 | Kimura et al. | 204/1 S |
| 4,272,329 | 6/1981 | Hetrick et al. | 204/195 S |
| 4,272,330 | 6/1981 | Hetrick | 204/195 S |
| 4,272,331 | 6/1981 | Hetrick | 204/195 S |

Primary Examiner—T. Tung
Attorney, Agent, or Firm—Peter Abolins; Clifford L. Sadler

[57] ABSTRACT

This specification discloses a step function lean burn sensor for determining the partial pressure of oxygen in an exhaust gas. Such a measurement is useful for air fuel ratio control in an internal combustion engine. This device uses the electrical properties of an electrochemical pump cell to determine the step function output. The device utilizes the qualitative nature of the current-voltage characteristic of the pump cell to reduce requirements on cell fabrication.

13 Claims, 6 Drawing Figures

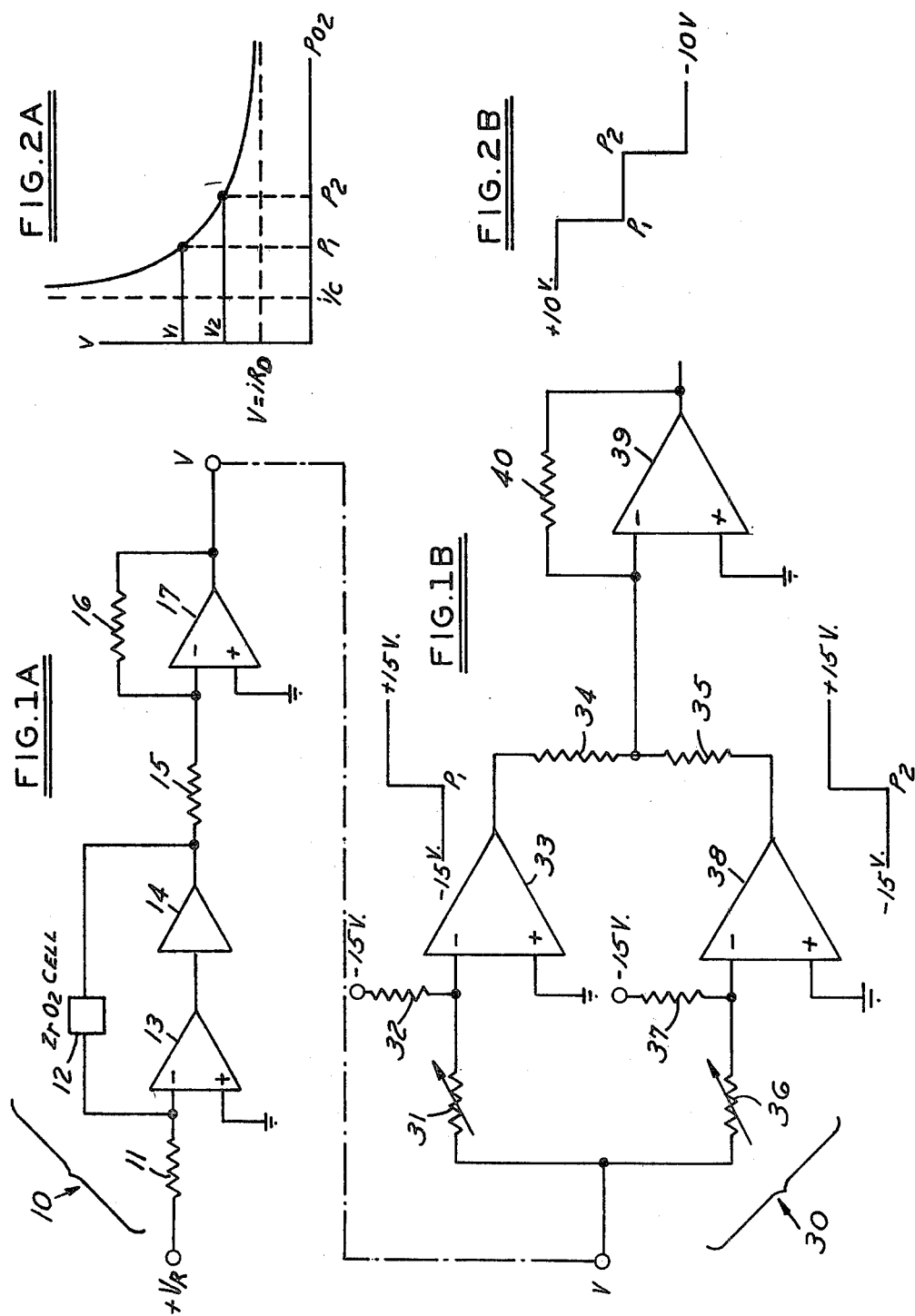

STEP FUNCTION LEAN BURN OXYGEN SENSOR

BACKGROUND OF THE INVENTION

1. Field of the Invention

This invention relates to determining the concentration of oxygen in a gaseous atmosphere.

2. Prior Art

U.S. Pat. Nos. 3,907,657 Heijne and 3,514,377 to Spacil et al relate to the measurement of oxygen ($O_2$) concentrations using solid electrochemical devices. For applications at elevated temperatures (>500° C.), for example, as might be encountered in the exhaust gases of furnaces or automobiles, the active material in these devices may be ceramic zirconium dioxide suitably adapted for the conduction O= ions. Electrochemical cells made from this material are suitable at elevated temperatures for oxygen sensing and pumping applications.

The mode of operation of the Heijne device can be described as an oxygen counting mode in which oxygen partial pressure is determined on a sampling basis. A constant current (or equivalent means) is applied to an electrochemical cell which forms part of the enclosure of a volume for a period of time, $t_p$, for the purpose of electrochemically pumping out most of the oxygen from that volume. The ambient atmosphere had established itself within the volume prior to the pump out, by means of a leak. An additional electrochemical cell, which serves as a sensor of the reduced oxygen partial pressure within the volume and which also constitutes a portion of the enclosure, provides a signal indicating when oxygen has been sufficiently depleted from the volume (see FIG. 4 of Heijne). Knowing the temperature, enclosed volume and the pump out current and time allows one to calculate the number of oxygen molecules within the enclosure from the ideal gas law. The number of oxygen molecules is in turn proportional to the desired oxygen partial pressure. If a constant pump current is used, the pump out time $t_p$ is proportional to the oxygen partial pressure. If a constant current is not used, then the integral of the pump out current over the pump out time is proportional to the oxygen partial pressure.

The Heijne device can provide an output which is linearly proportional to the oxygen partial pressure. This is superior, for example, to single oxygen concentration cells used as sensors which give an output (EMF) proportional to the natural logarithm of the oxygen partial pressure ln ($P_{O_2}$).

A potential disadvantage of the Heijne device is response time. For this measurement procedure, the leak connecting the ambient to the enclosed volume must be small so that during the pump out of oxygen, no significant amount of oxygen leaks into the volume to cause an error in the count of molecules (i.e., to erroneously increase $t_p$). However, if the leak is made small, it may take a long time, $t_v$, for the ambient to reestablish itself within the volume after a pump out. If the changes in the oxygen partial pressure in the ambient occur rapidly with respect to this refill time, the device would not be able to follow these changes in repetitive operation.

U.S. Pat. Nos. 3,923,624 to Beckmans et al, 3,654,112 to Beckmans et al, and 3,907,657 to Heijne et al describe tubular ceramic structures for measuring and controlling the composition of oxygen in a carrier gas. In some cases a pump cell and a sensor cell are used. U.S. Pat. Nos. 3,923,624 and 3,654,112 teach devices to be used primarily to dose a gas with oxygen to a constant partial pressure. Measurement of the dosed gas is made by a standard technique using a zirconium dioxide oxygen concentration cell to be sure that the dosed gas contains the correct amount of oxygen. The sensitivity of the concentration cell to the oxygen partial pressure is low, being proportional to ln ($P_{O_2}$). However, various types of automobile engines, e.g., diesel, do not require that much sensitivity when determining oxygen concentration for use in engine control. Since less sensitivity is acceptable, the additional sensitivity represents an undesirable additional expense. It would be desirable to reduce the cost of the oxygen sensor by not providing more accuracy than is required.

In the case of the teachings of U.S. Pat. No. 3,698,384 to Jones, the purpose is to measure oxygen partial pressure in a feedgas. This is done by measuring an electrochemical cell pumping current while holding the sensor cell voltage a constant. However, to achieve a result in the disclosed open ended tubular structure made from zirconium dioxide the flow rate of the feedgas must be kept constant. If the flow rate should attempt to vary, there is a relatively elaborate flow control circuit to keep the flow rate a constant. This scheme, which also employs a reference atmosphere is relatively unsuitable for application in an auto exhaust where the exhaust flow rate would change substantially with RPM.

U.S. Pat. Nos. 3,347,735 to McKee and 3,857,771 to Sternberg both describe oxygen sensing procedures or devices wherein the taking of a first derivative of an output signal either determines the oxygen partial pressure or can yield information on the medium which contains the oxygen. Neither device would be suitable for the continuous or repeated determination of the oxygen partial pressure in a variable, high temperature environment like that occurring in an automotive exhaust. U.S. Pat. Nos. 3,948,081; 3,738,341 and 4,112,893 relate to oxygen sensors and associated electrical circuitry which are a typical oxygen concentration cell type. These patents discuss external circuitry which may enhance the operation of such sensors under various conditions.

An important application of high temperature oxygen sensors is in the determination of the stoichiometric air fuel mixture in the exhaust gases of hydrocarbon fired furnaces or engines such as automobile internal combustion engines. The stoichiometric mixture is one in which the mass of air present contains just enough oxygen to react with the mass of hydrocarbons present so that there is the minimum amount of both oxygen and hydrocarbons remaining. For common automotive gasoline, the air fuel ratio A/F(=mass of air/mass of fuel) at the stoichiometric point is approximately 14.6. If, for example, an engine were running lean of stoichiometry (A/F>14.6) there would be an excess of air in the "charge" burned in the cylinder and the exhaust gas would contain a substantial oxygen partial pressure. If rich operation were occurring (A/F>14.6), the exhaust gas would contain unreacted or partially reacted hydrocarbons and very low oxygen partial pressure. In particular, the equilibrium oxygen partial pressure in the exhaust gas can change by a great amount (as much as 20 orders of magnitude) as one moves from lean to rich operation. This large change forms the basis for detecting the stoichiometric air fuel ratio with an exhaust gas oxygen sensor. The electrical output of such a sensor can then be fed back to an electrically controllable carburetor or fuel injection system for maintaining engine operation always at the stoichiometric point. Depending on engine type operation at this point frequently offers a reasonable compromise for minimizing regulated exhaust gas emissions and maximizing engine performance.

There are known high temperature oxygen sensors utilizing oxygen electrochemical concentration cells (usually made from zirconium oxide) and requiring the use of a reference atmosphere (usually air) are are suitable for determining the stoichiometric air fuel ratio in a high temperature automotive environment. These devices given an output (EMF) proportional to the natural logarithm of the oxygen partial pressure. Despite their low sensitivity to oxygen partial pressure, the large change in oxygen partial pressure at the stoichiometric point allows their useful implementation.

For some engines it is useful to operate lean of the stoichiometric A/F for the purpose of reducing fuel consumption. Oxygen partial pressure varies in a systematic way in the lean region and this can form the basis for determining lean A/F. Knowledge of lean A/F would be useful to fully implement a lean burn engine strategy which would maximize fuel economy and engine performance and minimize regulated emissions. However, the variation in oxygen partial pressure in the appropriate lean A/F region, e.g., $16 < A/F < 20$, is not large, (in comparison to the changes occurring near stoichiometry) so that suitable oxygen sensors with sensitivities greater than the natural logarithm of oxygen partial pressure are desirable for accurate measurement in the desired A/F range. For some automobile engines a step function output may provide sufficient sensitivity, as long as the step occurred within the desired lean A/F range. Known step function outputs occur at stoichiometry, but not at other A/F values. These are some of the problems this invention overcomes.

Also known is a patent application entitled "Steady State Mode Oxygen Sensor", Ser. No. 126,606, filed on Mar. 3, 1980 by the inventors of this invention, which discloses quantitative measurement of oxygen partial pressure in exhaust gases. In accordance with that patent application, a ceramic electrochemical structure with associated external circuitry is capable of measuring oxygen concentration in a high temperature surrounding environment such as may be found in an automotive exhaust. The external circuitry provides an electrical output whose magnitude is proportional to the percentage of gaseous oxygen. The structure includes two oxygen ion ($O=$) conducting electrochemical cells, a pump cell and a sensor cell, which in part provide the enclosing structure of a nearly enclosed volume. A portion of the remaining structure can be a hollow ceramic tube. The cells are attached to the end faces of the tube. A small aperture in the enclosing structure allows the ambient atmosphere, containing oxygen in a percentage to be determined, to leak into the volume.

In operation, the external circuitry causes a voltage to be applied to the pump cell with a propoer polarity to electrochemically pump oxygen out of the volume and return it to the ambient. After a brief transient period, a steady state is reached where the rate at which oxygen is pumped from the volume is equaled at the rate at which oxygen is diffusing into the volume by means of the aperture. Under this steady-state condition, the oxygen partial pressure within the volume is reduced from that in the ambient causing an EMF to develop across the electrodes of the sensor cell. Experimentally, it is found that if one causes the pump cell current to be continuously adjusted so that the sensor cell EMF if always a constant, then the magnitude of the pump cell current is linearly proportional to the percentage of oxygen in the ambient atmosphere. This linear relationship is the basis of sensor operation.

The above described oxygen sensor requires two Nernst cells, the pump cell and the sensor cell. It would be advantageous to develop a circuit which requires only one Nernst cell thus obviating the need for the seond cell and the associated seals coupling the cell to an enclosed volume. Further, the above devices disclosed operate on quantitative electrical measurements. As a result, components in such a system are relatively more critical than a system which would operate on qualitative electrical characteristics. For example, a step function output positioned at a desired lean A/F operating point can be classified as a qualitative signal and yet provide a sufficiently accurate output for certain engine types. These are some of the problems this invention overcomes.

SUMMARY OF THE INVENTION

In accordance with an embodiment of this invention, a step-function oxygen sensor is described whose output can adopt three values in a stepwise manner at particular values of oxygen partial pressure. Those values can be preset by means of external circuitry attached to the sensor. The device would be of advantage in applications which do not require proportional sensing of oxygen partial pressure but only an indication of being within a certain range (one output value) or at pressures greater than (the second output value) or less than (the third output value) those in the range. With additional circuitry, the concept can be expanded to have additional output steps for additional ranges of oxygen partial pressure. The sensor requires only a single oxygen concentration cell and operates on the qualitative nature of current-voltage characteristics of the zirconium dioxide cells thus reducing requirements on electrode fabrication and zirconium dioxide preparation. The device operates at elevated temperatures on the order of 800° C.

An electrochemical apparatus in accordance with an embodiment of this invention includes a solid electrochemical pump cell and an external circuit. The zirconium dioxide cell is attached to additional ceramic material to define an enclosed volume having a leak orifice and is driven by the external circuit.

BRIEF DESCRIPTION OF THE DRAWINGS

FIG. 1a is a schematic drawing of a first portion of a circuit for determining oxygen concentration in accordance with an embodiment of this invention.

FIG. 1b is a second portion of a circuit for determining oxygen concentration in accordance with an embodiment of this invention, the input being adapted to receive the output of the circuit of FIG. 1a.

FIG. 2a is a graphical representation of oxygen partial pressure versus voltage of the output of the circuit of FIG. 1a.

FIG. 2b is a graphical representation of oxygen partial pressure versus voltage for the output of the circuit of FIG. 1b.

DETAILED DESCRIPTION OF THE INVENTION

Figure 4:
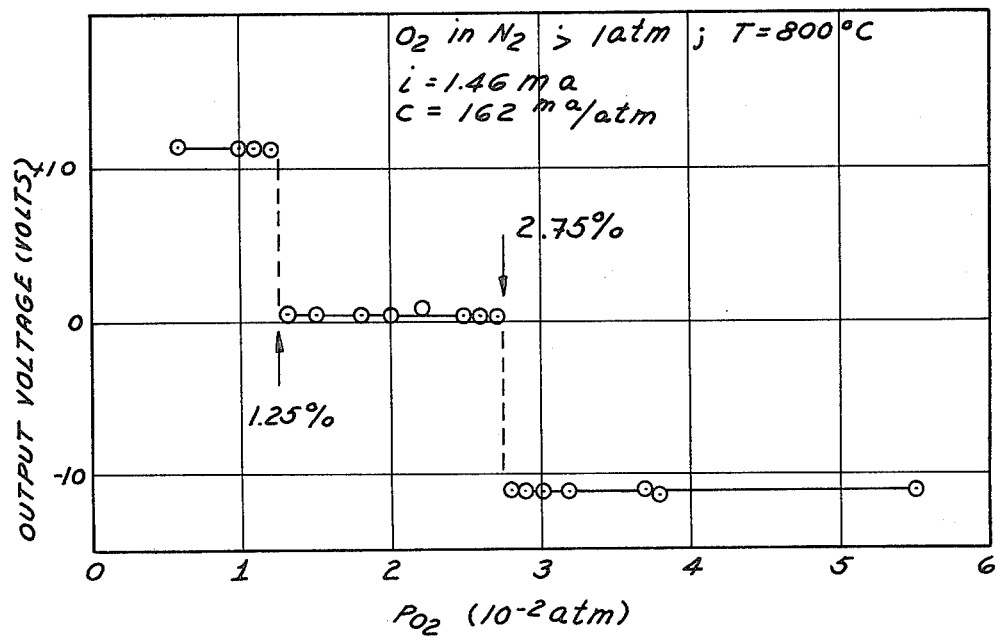
FIG. 4 is a graphical representation similar to FIG. 2b including experimental derived data.

Referring to FIG. 1a, an oxygen responsive circuit 10 includes a reference voltage $V_R$ coupled through a resistor 11 to the negative input of an amplifier 13. The positive input of amplifier 13 is grounded, and the output is coupled to the input of an amplifier 14. The output of amplifier 14 is coupled through a resistor 15 to the negative input of an amplifier 17. The positive input of amplifier 17 is grounded. The output of amplifier 17 is coupled through a resistor 16 to the negative input of amplifier 17. A zirconium dioxide electrochemical pumping cell 12 is coupled between the output of amplifier 14 and the negative input of amplifier 13.

Figure 3:
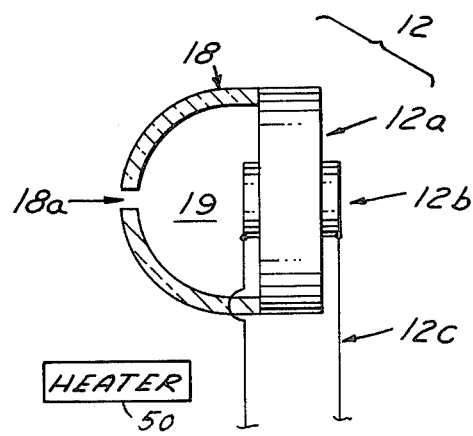
FIG. 3 is a schematic representation of the oxygen sensor including an electrochemical cell and attached structure.

Referring to FIG. 3, the structure of electrochemical pump cell 12 includes an ionically conducting platelet 12a sandwiched between electrical contacts 12b whereby an electrical current can be applied to the platelet to cause oxygen pumping by means of two lead wires 12c. The device further includes an associated enclosing tube 18 having a leak orifice 18a therein for establishing communication between the ambient and the enclosed volume 19. A heater 50 is positioned adjacent electrochemical pump cell 12 and maintains a sufficiently narrow temperature range to achieve a desired accuracy.

Referring to FIG. 1b, an input voltage is coupled from the output of amplifier 17 from FIG. 1a to a combination of resistors 31 and 36. Resistor 31 is coupled to the negative input of an amplifier 33 which has a positive input grounded. A reference voltage of minus 15 volts is coupled to a resistor 32 to the negative input of amplifier 33. The output of amplifier 33 is connected through a resistor 34 to the negative input of an amplifier 39. Similarly, resistor 36 is connected to the negative input of an amplifier 38 which has a positive input grounded. A voltage of $-15$ volts is applied to the negative input of amplifier 38 through a resistor 37. The output of amplifier 38 is coupled through a resistor 35 to the negative input of amplifier 39. The positive input to amplifier 39 is grounded, and the output of amplifier 39 is coupled through a resistor 40 to the negative input of amplifier 39.

FIG. 2b shows the characteristic output voltage at the output of amplifier 39. When the zirconium dioxide cell is attached to the leaky structure and used as an oxygen pump, it has been shown that the current-voltage characteristics of the pump volume combination is approximately given by the following equation:

$$v = iR_D - V_o \ln\left(1 - \frac{i}{i_s}\right)$$

where
v = voltage across Nernst cell
i = current through cell
$R_D$ = device resistance ($\simeq 30\omega$)

$$V_o = \frac{kT}{4e}$$

and
$i_s = CP_{O_2}$ where C is a constant and $P_{O_2}$ is the $O_2$ partial pressure external to the leaky $ZrO_2$ structure. If current is controlled at some constant value i, then, schematically, V is shown as a function of $P_{O_2}$ in FIG. 2a.

Cell voltage V can be compared to a reference voltage ($V_1$ in FIG. 2a) to create a substantial voltage step in an external circuit at pressure $P_1$. Further, several reference voltages $V_1, V_2 \ldots V_N$ can be used to create a sequence of voltage steps at pressures $P_1, P_2 \ldots P_N$.

From FIG. 2a it is seen that if $P_1$ is only slightly greater than i/C, high sensitivity will result. Switching at $P_1$ will then have high noise immunity. The current i, therefore, should be as large as possible, but such that i/C is less than the lowest pressure of interest. The structure of the cell and the enclosing structure (the size of the leak aperture in particular) can be adjusted to modify the value of $i_s$ and thereby shift the characteristic curve of FIG. 2A to a favorable position for the oxygen pressure range of interest.

In the device shown in FIGS. 1a and 1b, two voltage steps are produced and summed to yield the output characteristic of FIG. 2b. Amplifier 13 and amplifier 14 serve as a constant current source and produce a voltage-pressure curve where the voltage is (see FIG. 2a) amplfied by amplifier 17. The output voltage, V, is compared to two reference voltages $V_1, V_2$ by amplifiers 33 and 38; the resulting voltage steps are summed by amplifier 39 to obtain the desired output (see FIG. 2b). Threshold pressures are determined by adjusting input resistors 31 and 36 on amplifiers 33 and 38. Current through the pump cell 12 was determined by adjusting $V_R$, but also could have been obtained from a fixed bias and potentiometer.

The data of FIG. 4 show results where the device was set up to detect oxygen in the interval $1.25 \times 10^{-2}$ atm $< P_{O_2} < 2.75 \times 10^{-2}$ atm (an interval of $1.5 \times 10^{-2}$ atm).

The current of 1.46 mA would be suitable for switching at $O_2$ pressure in excess of $9 \times 10^{-3}$ atm. The pressure interval required for switching was less than $\simeq 0.1 \times 10^{-2}$ atm and was independent of whether $P_{O_2}$ was increasing or decreasing. This switching interval is suitable for intended applications, but could be improved by suitable latch circuitry on the amplifiers.

Accordingly, the combination of oxygen responsive circuit 10 and step function circuit 30 produce a sensitive lean burn air fuel sensor capable of accurate measurements for the operating ranges of engines such as diesel. The device has a relatively simple construction in comparison to those known and can be made small enough to be put on the end of a spark plug.

The particular switching pressures $P_1$ and $P_2$ shown in FIG. 2a can be controlled by bias adjustments of step function circuit 30. The three valued output shown in FIG. 2b provides an easily measurable signal specifying whether the air fuel ratio is above ($-10$ volts) or below ($+10$ volts) a desirable working range of interest, shown as zero voltage between partial pressure $P_1$ and $P_2$. Using an electrically controlled fuel injection or carburetion system such aan output signal is available for feedback control of air/fuel in any of these regions. Further, in principle, the three level outputs can be expended to more levels so that control within a variety of air/fuel regions would be possible. That is, one skilled in the art can expand the circuitry of FIG. 1 to include additional amplifiers and reference voltages to produce an output having multiple steps. Thus, the voltage at each step would indicate a particular range of oxygen partial pressure.

Typical components for amplifiers 13, 17, 33, 38 and 39 is integrated circuit model 741 produced by Texas Instruments, for amplifier 14 it is integrated circuit MC1438. Typical values also include resistor 11, 2.7 k ohms; resistor 15, 10 K ohms; resistor 16, 47 K ohms; resistors 31 and 36, 2 K ohms; resistors 32 and 37, 15 K ohms; resistors 34 and 35, 22 K ohms; resistor 40, 10 k ohms.

Various modifications and combinations of the disclosed embodiment will no doubt occur to those skilled in the art. For example, the particular integrated circuits and the values of the resistors and voltages may be varied from that disclosed herein. These and all other embodiments which basically come within the scope of this invention as defined in the appended claims.

We claim:

1. An electrochemical apparatus for making a measurement of oxygen partial pressure in an ambient environment including other gaseous materials, said electrochemical apparatus including:
   a single solid electrochemical pump cell formed of a platelet of solid ionic conductors capable of conducting oxygen ions and including two electrode layers attached to opposing faces of said platelet, and lead wires attached to each of said electrodes for providing electrical coupling to said pump cell;
   a leaky structure coupled to said electrochemical pump cell having an enclosed casing defining an enclosed volume and a leak orifice coupling the enclosed volume to the ambient;
   an external circuit means coupled to said pump cell for applying a current to said pump cell so that oxygen can be withdrawn from the enclosed volume thereby providing an electrical output indicative of oxygen partial pressure;
   said external circuit means including:
   a constant current source means coupled to said electrochemical pump cell thereby generating said electrical output wherein a voltage, V, is a function of the oxygen partial pressure;
   a first reference voltage means coupled to said constant current source means for producing a first step voltage output with the step occurring at a first output voltage related to a first oxygen partial pressure;
   a second reference voltage means coupled to said constant current means for producing a second step voltage output with the step occurring at a second output voltage related to a second oxygen partial pressure;
   an output means coupled to said first and second reference voltage means for generating a voltage step output having at least three voltage levels with steps occurring at said first and second partial pressure of oxygen thus indicating the relative magnitude of the oxygen partial pressure with respect to said first and second oxygen partial pressures.

2. An electrochemical apparatus as recited in claim 1 wherein said constant current source includes:
   an input resistor means for applying an input voltage; and
   a first amplifier means coupled to said input resistor means and said electrochemical pump cell so as to apply a constant current through said electrochemical pump cell.

3. An electrochemical apparatus as recited in claim 2 wherein said constant current source further includes a second amplifier coupled to said first amplifier for amplifying the output of said first amplifier.

4. An electrochemical apparatus as recited in claim 2 wherein said first reference voltage means includes:
   a third amplifier means coupled to said constant current source means and having a variable input means for adjusting the magnitude of said voltage, V, so that voltage, V, can be compared to a first reference voltage and an output from said third amplifier means has a step when said first reference voltage is equal to the adjusted magnitude of voltage, V.

5. An electrochemical apparatus as recited in claim 4 wherein said second reference voltage means includes:
   a fourth amplifier means coupled to said constant current source means and having a variable input means for adjusting the magnitude of said voltage, V, so that voltage, V, can be compared to a second reference voltage and an output from said fourth amplifier means has a step when said second reference voltage is equal to the adjusted magnitude of voltage, V.

6. An electrochemical apparatus as recited in claim 5 wherein said output means includes:
   a fifth amplifier means coupled so as to receive the output of said third and fourth amplifier means and to produce an output voltage having a first step where the output of said third amplifier means has a step and a second step where the output of said fourth amplifier means has a step.

7. An electrochemical apparatus as recited in claim 6 further comprising a heater means adjacent to said electrochemical pump cell to maintain a temperature range sufficiently small to achieve a desired accuracy.

8. A method of measuring oxygen partial pressure in an ambient environment including other gaseous materials including the steps of:
   passing a current through a single solid electrochemical pump cell formed of a platelet of solid ionic conductors capable of conducting oxygen ions coupled to a leaky structure having an enclosed casing defining an enclosed volume and a leak orifice for communication with the ambient environment, so that gaseous oxygen is withdrawn from the enclosed volume and returned to the ambient;
   generating a first step voltage as a function of the current;
   generating a second step voltage as a function of the current; and
   combining the first and second step voltages to produce an output voltage indicative of the oxygen partial pressure.

9. A method of measuring oxygen partial pressure as recited in claim 8 wherein the step of passing a current includes maintaining a constant magnitude for the current.

10. A method of measuring oxygen partial pressure as recited in claim 9 wherein the step of generating a first step voltage includes:
   comparing the magnitude of the voltage output from the electrochemical pump cell to a first reference voltage; and
   adjusting the magnitude of the voltage output so that the voltage step occurs as a function of a first oxygen partial pressure.

11. A method of measuring oxygen partial pressure as recited in claim 10 wherein the step of generating a second step voltage includes:
- comparing the magnitude of the voltage output from the electrochemical pump cell to a second reference voltage; and
- adjusting the magnitude of the voltage output so that the voltage step occurs as a function of a second oxygen partial pressure.

12. A method of measuring oxygen partial pressure as recited in claim 11 wherein the step of combining the first and second step voltages includes:
- generating a three level, two step voltage function having a first step transition as a function of the first oxygen partial pressure and a second step transition as a function of the second oxygen partial pressure thus indicating the relative magnitude of the oxygen partial pressure in the ambient environment with respect to the first and second oxygen partial pressures.

13. A method of measuring oxygen partial pressure as recited in claim 12 wherein the steps of adjusting the magnitude of the voltage output includes:
- varying the magnitude of a first resistor so that a voltage step occurs as a function of the first oxygen partial pressure; and
- varying the magnitude of a second resistor so that a voltage step occurs as a function of the second oxygen partial pressure.

* * * * *